United States Patent
Büeler et al.

(10) Patent No.: US 8,887,734 B2
(45) Date of Patent: Nov. 18, 2014

(54) CONTROL PROGRAM FOR CONTROLLING ELECTROMAGNETIC RADIATION FOR CROSS-LINKING EYE TISSUE

(75) Inventors: Michael Büeler, Zurich (CH); Michael Mrochen, Eglisau (CH)

(73) Assignee: IROC Innocross AG, Zug (CH)

( * ) Notice: Subject to any disclaimer, the term of this patent is extended or adjusted under 35 U.S.C. 154(b) by 678 days.

(21) Appl. No.: 13/063,178

(22) PCT Filed: Sep. 10, 2009

(86) PCT No.: PCT/EP2009/006579
§ 371 (c)(1),
(2), (4) Date: Aug. 1, 2011

(87) PCT Pub. No.: WO2010/028830
PCT Pub. Date: Mar. 18, 2010

(65) Prior Publication Data
US 2011/0301524 A1    Dec. 8, 2011

(30) Foreign Application Priority Data

Sep. 11, 2008 (DE) .......................... 10 2008 046 834

(51) Int. Cl.
*A61B 19/00*    (2006.01)
(Continued)

(52) U.S. Cl.
CPC ............. *G06F 19/3437* (2013.01); *A61B 3/107* (2013.01); *G06F 19/3481* (2013.01); *A61F 2009/00872* (2013.01)
USPC .................. 128/898; 606/5; 607/88; 351/212

(58) Field of Classification Search
USPC ....................... 607/88–92; 606/4–6; 128/898; 351/205–212; 700/1, 28
See application file for complete search history.

(56) References Cited

U.S. PATENT DOCUMENTS 5,163,934 A * 11/1992 Munnerlyn ........................ 606/5
5,740,815 A * 4/1998 Alpins ........................... 128/897

(Continued)

FOREIGN PATENT DOCUMENTS

DE    10 2004 033 819    2/2006
WO    WO 02/07660    1/2002
(Continued)

OTHER PUBLICATIONS

PCT/ISA/220, "Notification of Transmittal of the International Search Report and the Written Opinion of the International Searching Authority, or the Declaration" for PCT/EP2009/006579 (in German) (3 pgs.), Mar. 18, 2010.
(Continued)

*Primary Examiner* — Ahmed Farah
(74) *Attorney, Agent, or Firm* — John C. Pokotylo; Straub & Pokotylo

(57) ABSTRACT

A control program for controlling a source of electromagnetic radiation, with which a cross-linking in eye tissue of a patient is implemented by means of a photosensitiser introduced into the tissue in order to bring about a change in the eye tissue with reference to its form and/or one of its mechanical properties, the control program having been produced with the following steps:
a) measurement data with reference to the patient and the eye are acquired,
b) with the measurement data and treatment parameters, which involve a predetermined auxiliary control program for controlling the source of electromagnetic radiation, an outcome with reference to the change in the eye tissue obtained with these treatment parameters is simulated in a computer,
c) the change simulated in this way is compared with a change in the eye tissue to be achieved,
d) when step c) yields a sufficient agreement between the simulated change and the change in the eye tissue to be achieved, the auxiliary control program applied in step b) is chosen as the control program to be generated, and
e) when in step c) the comparison does not yield a sufficient agreement between the simulated change and the change in the eye tissue to be achieved, at least one of the treatment parameters in step b) is/are modified and steps b), c) and d) are then performed again therewith.

12 Claims, 3 Drawing Sheets

(51) Int. Cl.
*A61B 18/18* (2006.01)
*G06F 19/00* (2011.01)
*A61B 3/107* (2006.01)
*A61F 9/008* (2006.01)

(56) References Cited

U.S. PATENT DOCUMENTS

| | | | |
|---|---|---|---|
| 5,827,264 A * | 10/1998 | Hohla | 606/5 |
| 5,843,070 A * | 12/1998 | Cambier et al. | 606/5 |
| 5,891,131 A | 4/1999 | Rajan et al. | |
| 6,530,917 B1 * | 3/2003 | Seiler et al. | 606/5 |
| 7,175,278 B2 * | 2/2007 | Chernyak et al. | 351/246 |
| 7,237,898 B1 | 7/2007 | Hohla et al. | |
| 7,544,194 B2 * | 6/2009 | Mrochen et al. | 606/5 |
| 2007/0161972 A1 | 7/2007 | Felberg et al. | |
| 2008/0033408 A1 * | 2/2008 | Bueler et al. | 606/5 |
| 2008/0234668 A1 * | 9/2008 | Linnik et al. | 606/4 |

FOREIGN PATENT DOCUMENTS

| | | |
|---|---|---|
| WO | WO 2007/128581 | 11/2007 |
| WO | WO 2008/00478 | 1/2008 |

OTHER PUBLICATIONS

PCT/ISA/210, "International Search Report" for PCT/EP2009/006579 (in German) (4 pgs.), Mar. 18, 2010.

PCT/ISA/237, "Written Opinion of the International Searching Authority" for PCT/EP2009/006579 (in German) (6 pgs.), Mar. 11, 2011.

* cited by examiner

Depth of cornea

Computed increase in the polymer number in the cornea

Forecast criterion derived from measured pre-operative quantities

CONTROL PROGRAM FOR CONTROLLING ELECTROMAGNETIC RADIATION FOR CROSS-LINKING EYE TISSUE

BACKGROUND OF THE INVENTION

The invention relates to a control program for controlling a source of electromagnetic radiation with which a cross-linking in the eye tissue of the patient is implemented by means of a photosensitiser introduced into the tissue, and also to a process for producing such a control program, and to a process for ascertaining whether a patient is suitable for an ophthalmological treatment involving cross-linking of eye tissue by means of electromagnetic radiation and a photosensitiser.

The human eyeball is bounded by the outer tunic of the eyeball. By virtue of the intraocular pressure, the collagen-containing outer tunic of the eyeball is tightened and imparts an approximately spherical shape to the healthy eyeball. In the posterior eyeball region the outer tunic of the eyeball consists of the white sclera. Located in the anterior region is the cornea, which is transparent to visible light.

Deformations of the outer tunic of the eyeball can be the cause of defective vision. For example, one form of short-sightedness, axial myopia, can be the consequence of a scleral increase in the length of the eyeball. A surface of the cornea shaped as an ellipsoid can result in a form of astigmatism that is also designated as corneal distortion. Another disease of the cornea is designated as keratoconus. In the case of keratoconus, a progressive thinning and conical deformation of the cornea of the eye occur as a consequence of a pathological softening of the cornea. With the increasing bulging, the cornea becomes thinner below the centre. It may rupture and form a scar. This reduces visual acuity permanently. The causes of keratoconus are largely unknown even today. It occurs with increased frequency within a family, which speaks, inter alia, for a genetic predisposition. Atopic disorders such as allergic diseases constitute a further risk factor for the genesis of a keratoconus.

The conventional therapy for an advanced keratoconus provides for removing the diseased cornea and replacing it with an allogeneic graft. Such an operation is, however, an organ transplant, with the associated risks and complications. An appropriate visual faculty is frequently obtained only about two years after the operation. In addition, the transplantation of the cornea in the case of keratoconus mostly affects young persons, which is why the transplant has to function perfectly over a period of decades.

A therapy for keratoconus that is improved in contrast to this stabilises the cornea by cross-linking. The treatment permits a photochemical, non-tissue-ablating stabilisation or change of the biomechanical and biochemical properties of the cornea. The therapeutic principle is also applicable to other affected regions of the eye. A photosensitiser solution is introduced into the eye tissue to be changed and is exposed to a primary radiation. Electromagnetic radiation within the wavelength range from approximately 300 nm to 800 nm (UV-A radiation or visible light) is employed as primary radiation.

Appropriate apparatuses for treating the outer tunic of the eyeball are known from documents WO 2007/128581 A2 and WO 2008/000478 A1.

An apparatus according to WO 2007/128581 A2 serves for strengthening the sclera located in the posterior portion of the eye. In this case the primary radiation can act on the sclera through the interior of the eye or through pads resting against it from outside. By means of a photomediator or photosensitiser, a cross-linking is brought about in the sclera. As a result, a growth of the sclera is counteracted and a progression of the axial myopia is prevented.

Printed publication WO 2008/000478 A1 describes an irradiation system for biomechanical stabilisation of the cornea. Here too, in conjunction with a photosensitiser a cross-linking can be brought about on the cornea. The irradiation system offers the possibility of treating specific diseases such as keratoconus.

The change of the form and/or of mechanical properties of eye tissue, in particular of the cornea and generally of the sclera, by means of an introduced photosensitiser and electromagnetic radiation is well-known as such in the state of the art, in particular as mentioned above. With regard to the chemical composition of the photosensitiser, reference is made to the state of the art, also with regard to the type of electromagnetic radiation employed, in particular the suitable wavelengths in conjunction with certain photosensitisers.

However, complex dependences conflict with a routine use of cross-linking therapy on the eye tissue. The relationships between the doses employed and the effect thereof in the eye tissue are highly diverse. By way of dose in this sense there enter into consideration, in particular, the electromagnetic radiation with regard to its intensity as well as its distribution in space and time; the photosensitiser employed with regard to its chemical structure, concentration, and action in space and time.

The effects of different doses of these parameters on and in the eye tissue of a patient are very highly dependent on properties (measurement data) with reference to the patient. In this connection it is to be taken into account, in particular, that the effect of the cross-linking implemented with the radiation and the photosensitiser may also be undesirable and may go so far as to damage the eye tissue or the functioning of the eye.

The object underlying the invention is to make processes and control programs available with which an assessment of the effect of a cross-linking can be estimated as reliably as possible already in the run-up to a possible ophthalmological intervention.

SUMMARY OF THE INVENTION

To this end, the invention makes available a process for generating a control program for controlling a source of electromagnetic radiation, with which a cross-linking in the eye tissue of a patient is implemented by means of a photosensitiser introduced into the tissue in order to bring about a change in the eye tissue with reference to its form and/or at least one of its mechanical properties, with the following steps:
   a) measurement data with reference to the patient and the eye are acquired,
   b) with the measurement data and treatment parameters, which involve a predetermined auxiliary control program for controlling the source of electromagnetic radiation, an outcome with reference to the change in the eye tissue obtained with these treatment parameters is simulated in a computer,
   c) the change simulated in this way is compared with a change in the eye tissue to be achieved,
   d) when step c) yields a sufficient agreement between the simulated change and the change in the eye tissue to be achieved, the auxiliary control program applied in step b) is chosen as the control program to be generated, and
   e) when in step c) the comparison does not yield a sufficient agreement between the simulated change and the change in the eye tissue to be achieved, at least one of the treatment parameters in step b) is/are modified and steps b), c) and d) are then performed again therewith.

According to a preferred configuration, the invention provides that in step a) one or more of the following data are drawn upon by way of measurement data: the corneal topography of the eye of the patient; the shape of the posterior surface of the cornea; other shape properties of the anterior and/or posterior surface of the cornea, such as depressions or elevations; biomechanical properties of the cornea, such as the stability thereof; the thickness of the cornea; the length of the eye; the depth and/or the volume of the anterior chamber; results of wavefront measurements; the age, sex, hormonal status of the patient; the state of a given ectasia; habits (e.g. smoking) of the patient.

Another preferred configuration of the process provides that in step b) the auxiliary control program takes account of one or more of the following quantities: intensity of the irradiation with the electromagnetic radiation; concentration of the photosensitiser in the tissue; the osmotic characteristic of the photosensitiser; the irradiation-time; the period of application of the photosensitiser before the irradiation; the periods of application of the photosensitiser during the irradiation; the type of the electromagnetic radiation (e.g. continuous or pulsed), inclusive of the radiation parameters such as the wavelength; the keying-rate in the case of pulsed radiation; the spatial and temporal control of the radiation.

Moreover, the invention makes available a control program for controlling electromagnetic radiation for implementing a cross-linking in eye tissue, the control program having been generated with the following steps:

a') measurement data with reference to the patient and the eye are acquired, b') with the measurement data and treatment parameters, which involve a predetermined auxiliary control program for controlling the source of electromagnetic radiation, an outcome with reference to the change in the eye tissue obtained with these treatment parameters is simulated in a computer, c') the change simulated in this way is compared with a change in the eye tissue to be achieved, d') when step c') yields a sufficient agreement between the simulated change and the change in the eye tissue to be achieved, the auxiliary control program applied in step b') is chosen as the control program to be generated, and e') when in step c') the comparison does not yield a sufficient agreement between the simulated change and the change in the eye tissue to be achieved, at least one of the treatment parameters in step b') is/are modified and steps b'), c') and d') are then performed again therewith.

According to a particularly simple configuration of the invention, it is ascertained whether a patient is at all suitable for an ophthalmological intervention by means of cross-linking. To this end, the invention makes available a process for ascertaining whether a patient is suitable for an ophthalmological treatment involving cross-linking of eye tissue by means of electromagnetic radiation and by means of a photosensitiser, with the following steps:

a'') measurement data with reference to the patient and the eye are acquired, b'') with the measurement data and treatment parameters, which involve a predetermined auxiliary control program for controlling the source of electromagnetic radiation, an outcome with reference to the change in the eye tissue obtained with these treatment parameters is simulated in a computer, c'') at least one critical change in the eye tissue is predetermined, d'') the simulated change in the eye tissue is compared with the critical change in the eye tissue and e'') when the simulated change agrees sufficiently with the critical change it is established that the patient is not suitable for an ophthalmological treatment using the auxiliary control program.

In a further development, the auxiliary control program provides—before, at the same time as, or after the controlling of the source of electromagnetic radiation for the purpose of cross-linking—a (second) controlling of a source of electromagnetic radiation for the purpose of changing the eye tissue with reference to its form and/or at least one of its mechanical properties by photothermal action, photoablation and/or photodisruption. In particular, the stated source of electromagnetic radiation for photothermal action, photoablation and/or photodisruption may be a femtosecond laser or an excimer laser.

BRIEF DESCRIPTION OF THE DRAWINGS

Exemplary embodiments of the invention will be described in more detail in the following.

Shown are.

DETAILED DESCRIPTION

By the term 'cross-linking' in ophthalmology a photochemical influence exerted on eye tissue is understood. The change achieved by this influence may reside in the biomechanical and biochemical properties of the tissue, but in particular also in a change in the form of the tissue, in particular in its shape and/or curvature. A stabilisation of the tissue is also obtained by a cross-linking, i.e. a change in its mechanical elasticity. To this end, in a manner known as such a photosensitiser, i.e. a suitable chemical solution, is brought onto and into the eye tissue, which then together with the electromagnetic radiation brings about the photochemical processes in the tissue that are addressed under the keyword 'cross-linking'. In this connection the effect of the electromagnetic radiation, also called 'primary radiation', on and in the tissue is neither thermal nor photoablative nor photodisruptive.

The invention described in more detail in the following makes available a process with which the complex relationships between the diverse properties of the electromagnetic radiation employed (e.g. wavelength, intensity, distribution in space and time) as well as the diverse properties of the photosensitiser employed (e.g. chemical nature; concentration; dilution; osmotic properties; chronological sequence of application etc.) and the effect achieved thereby in the eye tissue, in particular in the cornea, can be determined at least approximately for each individual patient. The use of the invention in its full scope enables the acquisition of a control program with which electromagnetic radiation for the cross-linking can be introduced into the eye tissue. A control program in this sense includes the control, known as such in the state of the art, of optical means with which laser radiation can be directed, for example via mirrors and other imaging optical elements such as lenses etc., onto the eye to be treated, for example in the form of a so-called 'spot'—that is to say, a patch that is relatively small in relation to the overall dimensions of the eye (with a diameter within the mm range)—which is guided in relation to the eye in space and time in accordance with a predetermined program. In the state of the art other means are also known in order to introduce electromagnetic radiation into eye tissue in accordance with a desired program, such as, for example, rotating masks, moving diaphragms etc.

In particular, the irradiation system according to international patent application PCT/EP2007/005740 (aforementioned publication WO 2008/000478 A1) is capable of being employed as apparatus for realising the present invention and for steering electromagnetic radiation onto an eye. This known irradiation system for ophthalmological applications is assumed to be expressly known for the realisation of the present invention.

Figure 1:
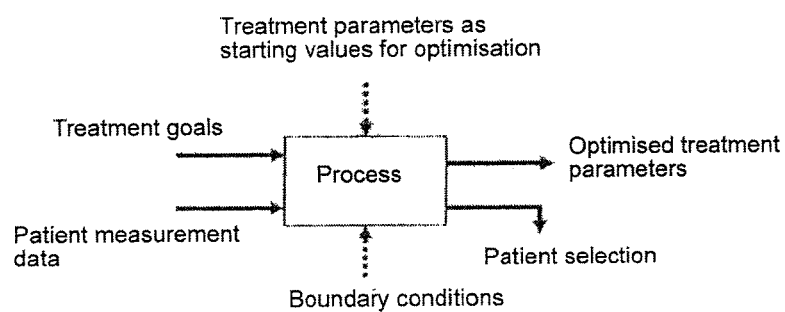
FIG. 1 schematically, a block diagram for the realisation of the invention in its full scope.

FIG. 1 illustrates schematically the input quantities for the process according to the invention for generating a control program, and the results obtained after implementation of the process. In its full realisation the process is iterative, i.e. starting from a relatively generally valid auxiliary control program this initial auxiliary control program is improved successively, loop by loop (that is to say, iteratively), until the properties of the control program generated in this way correspond to the desired expectations, taking account of the properties of the patient and his/her eye.

According to FIG. 1, "treatment parameters" as starting values for the optimisation are firstly input into the process for iteratively generating the stated control program. These treatment parameters involve, inter alia, the aforementioned initial auxiliary control program with which the iterative process can be started.

Further input data into the appropriately programmed computer executing the process are the "treatment goals". Treatment goals are, for example, the desired therapeutic changes in the form and/or in the mechanical properties of the eye tissue to be treated, in particular the cornea.

The "treatment parameters" in the stated sense include, in particular, the following quantities, which the auxiliary control program uses as data to be taken into account: intensity of the irradiation with the electromagnetic radiation; concentration of the photosensitiser in the tissue; the osmotic characteristic of the photosensitiser; the irradiation-time; the period of application of the photosensitiser before the irradiation; the periods of application of the photosensitiser during the irradiation; the type of the electromagnetic radiation (e.g. continuous or pulsed), inclusive of the radiation parameters such as wavelength; the keying-rate in the case of pulsed radiation; the spatial and temporal control of the radiation.

Further input data into the programmed computer executing the process are "patient measurement data". These are, in particular, the following data: the corneal topography of the eye of the patient; the shape of the posterior surface of the cornea; other shape properties of the anterior and/or posterior surface of the cornea, such as depressions or elevations; biomechanical properties of the cornea, such as the stability thereof; the thickness of the cornea; the length of the eye; the depth and/or the volume of the anterior chamber; results of wavefront measurements; the age, sex, hormonal status of the patient; the state of a given ectasia; habits (e.g. smoking) of the patient. The aforementioned data may be input, in each instance individually or in arbitrary combination, as "patient measurement data".

Moreover, the auxiliary control program initially accepts so-called "boundary conditions" as input data. These are, in particular, data relevant to safety, i.e. defaults that the program takes into account in the course of its execution, described in more detail further below, in order to avoid undesirable effects in the treated tissue. These are, in particular, cases of cell damage on the endothelium of the cornea and the avoidance of a so-called 'over-cross-linking' effect in the stroma. If on the basis of the input data, inclusive of the patient data, in the course of the simulation of the result of treatment brought about thereby the program comes to the conclusion that, for example, cell damage on the endothelium or an over-cross-linking is to be feared, this is communicated clearly to the user in the output data, in particular also in the form of a special warning.

Moreover, the "treatment goals" are input into the program, i.e. the changes in the eye tissue to be achieved with the cross-linking in order to achieve a therapeutic effect. The treatment goals accordingly consist in a desired change in the eye tissue with regard to its form (shape/curvature) and/or its biomechanical properties such as strength and stability.

One application to be given particular prominence is represented by treatment goals that are directed towards a selective biomechanical deformation of the cornea for the purpose of correcting cases of defective vision. In this case, changes of shape of the cornea or tissue structure are predetermined by the treatment goals and are taken into account in the simulation by corresponding target quantities of the auxiliary control program. This change in the form or in the mechanical properties of the eye tissue for the purpose of correcting cases of defective vision advantageously goes beyond the purely photochemical cross-linking and also includes a photothermal action, a photoablation and/or photodisruption, induced by electromagnetic radiation (corrective irradiation). Advantageously this expansion does not require any elaborate conversions in respect of the irradiation system but can be obtained merely by a corresponding expansion of the control program. The auxiliary control programs, and hence ultimately also the control programs, can fit in the corrective irradiation temporally previous to, simultaneously with, or subsequent to the photochemical treatment of the tissue by cross-linking. In an expanded embodiment the (auxiliary) control program contains parameters and/or control signals for driving a femtosecond laser or an excimer laser for the corrective treatment.

Depending on the aforementioned input data into the initial auxiliary control program, the latter then begins to compute the effects in a manner depending on the input data. The computational goals in this case are, in particular: depth of keratocyte damage, the occurrence of the stated over-cross-linking and the associated tissue depth, the increase in mechanical strength depending on the tissue depth, a change in form of the irradiated tissue with regard to shape and curvature directly after the treatment, the temporal progression—taking place subsequent to the treatment—of the aforementioned changes with regard to strength and shape of the tissue (directly after the treatment these properties may present themselves otherwise than hours or days after the treatment).

One possibility for programming the control program consists in ascertaining empirically the relationship between the stated input data (that is to say, roughly stated: patient data; radiation data; photosensitiser data (for details, see above)) and the change (effect) achieved thereby in the eye tissue, and in saving said relationship in a kind of 'look-up table' in the program. This is possible by using both a plurality of suitable experimental animals and by using data that are acquired with a plurality of patients.

A further—where appropriate, complementary—possibility for simulating in the control program the respective effects (changes in the eye tissue) in a manner depending on the input data provides for drawing upon theoretical concepts. These are, in particular, physical models of the photopolymerisation process (the cross-linking) in the form of mathematical descriptions of the individual subprocesses. Such physical models enable, for example, the simulation of the diffusion of the photosensitiser solution into the eye tissue by means of the diffusion equations. The effect of the electromagnetic radiation can also be computed on the basis of a model, by the absorption of the photons in the tissue and in the photosensitiser solution being computed, specifically by means of absorption equations, known as such, in a manner depending on the effective cross-sections. Moreover, such theoretical processes, which are known as such, can be employed in order to simulate the change in form of the eye tissue in a manner depending on the change in mechanical strength achieved, for example by using the method of finite elements which is well-known in mechanics.

With these partially or entirely empirical aids the program computes the effect of the electromagnetic radiation, taking the input data into account, and then an estimate can be made, either in the program or by the user, as to whether the simulated change in the properties of the eye tissue agrees sufficiently with the desired therapeutic changes in the eye tissue. For the 'sufficient agreement', in each instance tolerance values with reference to the individual parameters can then be predetermined and then, if the deviation lies within the tolerance values, 'sufficient agreement' can be inferred. If a sufficient agreement is detected, the control program last used can then be drawn upon as the control program to be generated that is being sought for controlling the electromagnetic radiation, and the treatment of the patient can be implemented with it.

If the difference between the simulated result of the change in the eye tissue and the desired therapeutic change in the eye tissue lies outside the stated tolerance values, then the treatment parameters, for example the auxiliary control program employed for the next loop, are changed. For example, with regard to the photosensitiser, its concentration, temporal application, chemical nature etc. can be changed, or properties of the electromagnetic radiations employed in the simulation—such as, for example, irradiation intensity, irradiation-time, type of radiation (continuous or pulsed), inclusive of the appropriate keying-rate etc., the wavelength of the radiation, the distribution of the radiation in space and time—can be modified. The direction of the change of these input treatment parameters may also be predetermined in the program on the basis of empirical experience, for example in the case of the result of an over-cross-linking in the preceding loop the irradiation intensity and/or the photosensitiser concentration can be diminished.

As a result, the iterative process, where appropriate after passing through several simulation loops, provides optimised treatment parameters, inclusive of the control program for controlling the electromagnetic radiation, i.e. a program that involves all the significant parameters of the electromagnetic radiation, such as intensity, distribution in space and time, wavelength, keying-rate etc. The program also provides optimal values with reference to the parameters of the photosensitiser, such as chemical structure, concentration, temporal application, spatial application etc.

As a result of the iterative process in the computer that has been described, it may also emerge that the patient whose data are counted amongst the input data is not suitable for the ophthalmological treatment involving cross-linking. This is denoted in FIG. 1 by the keyword "patient selection".

Figure 2:
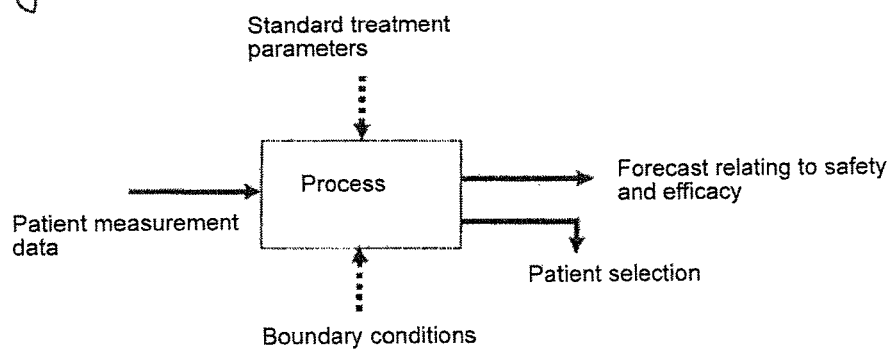
FIG. 2 schematically, a block diagram of the realisation of the invention in restricted scope.

FIG. 2 shows a simplified variant of the invention that makes it possible to judge for a given patient whether he/she is actually suitable for a treatment of the type under discussion here, involving cross-linking, specifically using predetermined standard treatment parameters. The process is then not iterative but consists of a single computational loop using the standard treatment parameters, the individual measurement data of the patient, and boundary conditions in the above sense. Hence, as above, the change in the eye tissue is then computed by simulation, and on the basis of the simulated outcome a statement is made as to whether the patient is suitable for a treatment involving cross-linking. For this, in particular the aforementioned boundary conditions are drawn upon, and it is established whether the result of the simulation attains critical values with regard to the boundary conditions.

Accordingly, for example, for a particular patient in the case of application of the standard treatment parameters a depth of keratocyte damage can result by simulation that forbids a treatment of the patient by cross-linking with the standard treatment parameters. In the case where the standard treatment parameters are employed, a change in curvature of the cornea in the course of the simulation can also result that is far removed from the desired treatment goal. For a user with relatively slight equipment in terms of hardware and software, without any possibility of changing the input treatment parameters, this enables a selection of patients who are suitable for the treatment. A restriction to the standard treatment parameters may also be demanded by an experience horizon of the operating surgeon or for licensing reasons.

Figure 3:
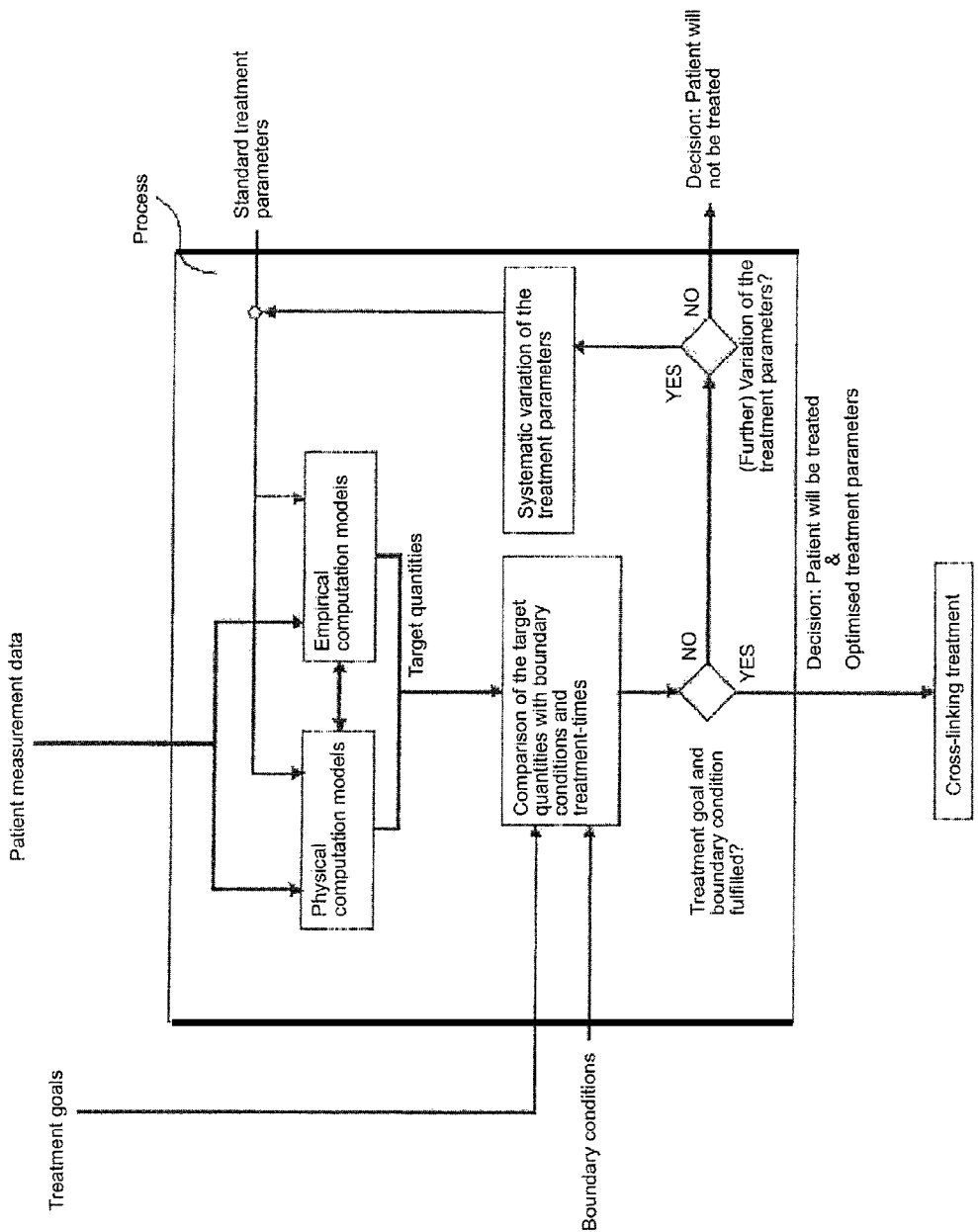
FIG. 3 a block diagram for illustrating the process according to the invention for generating a control program for the control of electromagnetic radiation in the course of a cross-linking.

FIG. 3 summarises, again schematically in a block diagram, the essential features of the generation of the control program for controlling the radiation for the cross-linking. The diagram illustrates, in brief, the processes described above for control-program generation. Explicit examples of the quantities stated in the diagram can be gathered from the following table.

| Quantity | Examples |
| --- | --- |
| Treatment depth | max. increase in strength, min. treatment-time, defined change of shape etc. |
| Patient measurement data | Topography of anterior and posterior surfaces of the cornea, biomech. stability of the cornea, thickness of the cornea, length of the eye, depth and volume of the anterior chamber, length of the eye, wavefront, age, sex etc. |
| Standard treatment parameters | Starting values for optimisation |
| Target quantities | Depth of keratocyte damage, increase in mechanical strength, change in shape/curvature of the tissue etc. |
| Boundary conditions | max. depth of keratocyte damage 100 microns away from endothelium, no over-cross-linking effect etc. |
| Optimised treatment parameters | Irradiation intensity, photosensitiser concentration, osmotic characteristic of the photosensitiser concentration, irradiation-time, photosensitiser application-time before irradiation, photosensitiser application intervals during irradiation, the type of |

| Quantity | Examples |
|---|---|
| | radiation (continuous or pulsed), wavelength, intensity distribution or irradiation pattern of the radiation etc. |

The processes represented, as well as the physical and empirical computation models, will be elucidated in more detail in the following.

The process starts from the patient-specific measurement data that are input into the physical and empirical computation models. The data record to be simulated is initially completed by the standard treatment parameters.

By way of treatment goals, one of the following goals or a combination of the following goals is specified to the process: maximisation of an increase in mechanical strength of the eye tissue, minimisation of a period of a treatment of the eye tissue, deformation of the eye tissue in accordance with a predetermined structure, and defined change of a refractive index in the eye tissue. Contrasted with these treatment goals are the increase in mechanical strength of the eye tissue computed by the simulation, the deformation of the eye tissue directly after the treatment, the deformation of the eye tissue in a manner depending on the period of the treatment or on the refractive index in the eye tissue. In this case, in particular the increase in mechanical strength and the refractive index are computed in a manner depending on a depth in the eye tissue. Furthermore, boundary conditions determined by safety are prescribed for the process. These rule out, for example, damage to keratocytes on an endothelium of the eye tissue and an effect of a cross-linking going too far (over-cross-linking) in the stroma of the eye tissue. The depth of the damage to the keratocytes computed by the simulation and the depth of the effect of the over-cross-linking are compared with these demanded boundary conditions.

Figure 4:
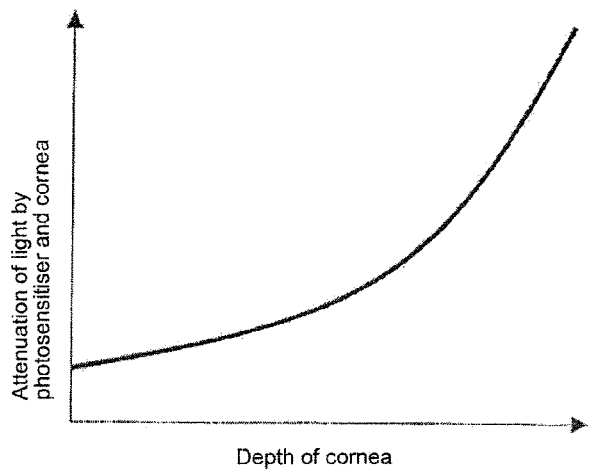
FIG. 4 schematically, an empirically observed relationship with regard to attenuation of light by photosensitiser and cornea as a function of a depth of the cornea.

The following physical models are taken as the basis for the computation. Firstly the diffusion of the photosensitiser with concentration c is computed in time-dependent manner. This is done in accordance with the following diffusion equation:

$$\frac{\partial c}{\partial t} = D\left(\frac{\partial^2 c}{\partial x^2} + \frac{\partial^2 c}{\partial y^2} + \frac{\partial^2 c}{\partial z^2}\right)$$

which is solved numerically, taking the surface geometry of the cornea into account. Hence the distribution of the photosensitiser is known. Now the absorption of the radiation by the cornea and the known distribution of the photosensitiser according to the wavelength-dependent Lambert-Beer law are determined, preferentially taking account of the empirically found relationship shown schematically in FIG. 4. In this connection the value, different from 0, of the attenuation of light in the case of vanishing depth of the cornea is caused by the adhesive film of the photosensitiser solution. Hence, in particular, the depth-dependent radiation intensity $I(t, x, y, z)$ is known. The validity of the parameters inserted into the light-attenuation law is, in addition, validated and updated in a manner depending on a current data stock derived from experimental tests on animal corneas. Now a physicochemical computation model finds application that specifies the polymer generation as a function of the local irradiction intensity $I(t, x, y, z)$ and the locally applied photosensitiser concentration $c(t, x, y, z)$. The local irradiation intensity in this case takes account of the computed attenuation of light by the adhesive film of the (residual) photosensitiser solution on the cornea. Consequently the generation of new collagen polymers by the interaction of UV radiation and photosensitiser is known.

Figure 5:
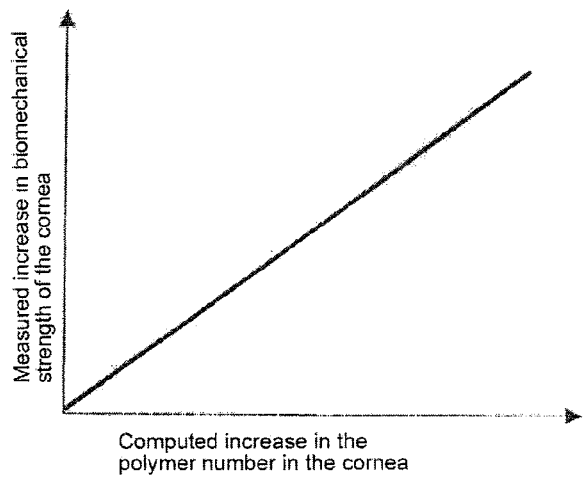
FIG. 5 schematically, a measured increase in a biomechanical strength of the cornea as function of a computed increase in the polymer number in the cornea.

Building upon this, empirical computation models find application that quantify the desired effect on the mechanical properties. This is done by the values of the polymer generation acquired from the physical computation models being linked with the values from stress/strain measurements in respect of pig corneas with varying cross-linking. FIG. 5 shows schematically the relationship found empirically between biomechanical strength and computed polymer number. A general tendency in this case is that a greater polymer generation results in a greater increase in strength, which is described quantitatively by the modulus of elasticity of the cornea.

Likewise building upon the results of the physical computation model with regard to the concentration $c(t, x, y, z)$ and the radiation intensity $I(t, x, y, z)$, the depth of keratocyte damage in the cornea is determined as one of the boundary conditions. In addition, tabulated values of the depth of keratocyte damage are present which were acquired in animal experiments.

Figure 6:
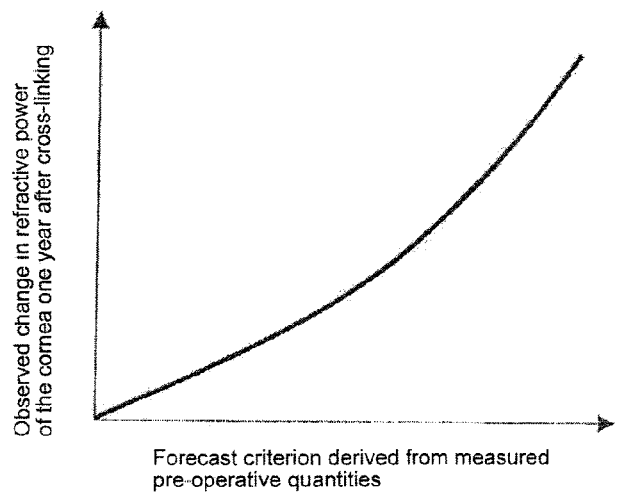
FIG. 6 schematically, an observed change in refractive power of the cornea one year after cross-linking as a function of a forecast criterion derived from measured pre-operative quantities.

A forecast concerning the change in curvature to be expected as one of the treatment goals is likewise simulated and is quantified by a numerical forecast criterion of the dioptre adjustment. In order to improve the sustainability of the forecast further, the forecast criterion and further pre-operative patient data are linked with changes in curvature already achieved, which were observed one year after implementation of the treatment in respect of a statistically significant plurality of treated patients. The linkage is given by an empirical function that is the result of a correlation analysis of the observed changes in curvature and of the pre-operative patient data. FIG. 6 shows schematically the empirical function that specifies the change in refractive power achieved after one year in a manner depending on the numerical forecast criterion.

If treatment goals or boundary conditions are not fulfilled, in the simplified process a decision against the treatment of the patient is made. In the full-scope realisation of the process shown in FIG. 3 the simulation is repeated on the basis of a systematic variation of the treatment parameters. This iterative process is terminated upon reaching an upper limit of iterations, likewise with the decision against the treatment of the patient, if the treatment goals or boundary conditions remain forecast by the simulation as inappropriate.

If the comparison of the simulated target quantities with the boundary conditions and treatment goals results in a predetermined agreement, the decision for the treatment of the patient is made. In this case the treatment parameters last employed in the simulation represent substantially the acquired control program.

The invention claimed is:

1. Process for iteratively generating a control program that controls electromagnetic radiation for cross-linking in eye tissue of a patient with a photosensitiser introduced into the eye tissue in order to bring about a change in the eye tissue with reference to at least one of (A) its form or (B) at least one of its mechanical properties, the process comprising:
   a) acquiring measurement data with reference to the patient and the eye;
   b) based on the measurement data and treatment parameters, the treatment parameters being parameters of a predetermined auxiliary control program for controlling a source of the electromagnetic radiation, obtaining a simulated change in the eye tissue the simulated change determined by a computer
   simulating a diffusion of the photosensitiser for the purpose of determining a distribution of the photosensitiser and
   determining a depth-dependent absorption of the radiation on the basis of the simulated distribution of the photosensitiser;
c) comparing the simulated change with a change in the eye tissue to be achieved;
d) if step c) yields a sufficient agreement between the simulated change and the change in the eye tissue to be achieved, choosing the auxiliary control program that includes the treatment parameters applied in step b) as the control program to be generated; and
e) if in step c) the comparison does not yield a sufficient agreement between the simulated change and the change in the eye tissue to be achieved, modifying at least one of the treatment parameters in step b) and repeating steps b), c) and d).

2. Process according to claim 1, characterised in that in step a) one or more of the following data are drawn upon by way of measurement data: a corneal topography of the eye of the patient; a shape of a posterior surface of the cornea; other shape properties of at least one of an anterior or posterior surface of the cornea, such as depressions or elevations; biomechanical properties of the cornea, such as the stability thereof; a thickness of the cornea; a length of the eye; at least one of a depth or a volume of an anterior chamber; results of wavefront measurements; an age, sex, hormonal status of the patient; a state of a given ectasia; habits of the patient.

3. Process according to claim 2, wherein at least one of the habits of the patient include smoking.

4. Process according to claim 1, characterised in that in step b) the treatment parameters include one or more of the following quantities: intensity of an irradiation with the electromagnetic radiation; concentration of the photosensitiser in the eye tissue; an osmotic characteristic of the photosensitiser; an irradiation-time; a period of application of the photosensitiser before the irradiation; periods of application of the photosensitiser during the irradiation; a type of the electromagnetic radiation, inclusive of radiation parameters such as wavelength; a keying-rate in a case of pulsed radiation; a spatial and temporal control of the radiation.

5. Process according to claim 4, wherein the type of electromagnetic radiation is continuous.

6. Process according to claim 4, wherein the type of electromagnetic radiation is pulsed.

7. Process according to claim 1, characterised in that in step b) the treatment parameters include one or more of the following quantities: intensity of an irradiation with the electromagnetic radiation; concentration of the photosensitiser in the eye tissue; an osmotic characteristic of the photosensitiser; an irradiation-time; a period of application of the photosensitiser before the irradiation; periods of application of the photosensitiser during the irradiation; a type of the electromagnetic radiation, inclusive of radiation parameters such as wavelength; a keying-rate in a case of pulsed radiation; a spatial and temporal control of the radiation.

8. Process according to claim 7, characterized in that in step a) habits of the patient are drawn upon by way of measurement data, wherein at least one of the habits of the patient include smoking.

9. Process according to claim 7, wherein the type of electromagnetic radiation is continuous.

10. Process according to claim 7, wherein the type of electromagnetic radiation is pulsed.

11. A non-transitory computer readable medium comprising a program stored thereon for determining parameters of a control program, the control program controlling a source of electromagnetic radiation for cross-linking in eye tissue of a patient with a photosensitiser introduced into the eye tissue in order to bring about a change in the eye tissue with reference to at least one of (A) its form or (B) at least one of its mechanical properties, the stored program to cause one or more processors to:
   a') acquire measurement data with reference to the patient and the eye;
   b') based on the measurement data and treatment parameters, the treatment parameters being parameters of a predetermined auxiliary control program for controlling a source of the electromagnetic radiation, obtain a stimulated change in the eye tissue by
      simulating a diffusion of the photosensitiser for the purpose of determining a distribution of the photosensitiser, and
      determining a depth-dependent absorption of the radiation on the basis of the simulated distribution of the photosensitiser;
   c') compare the simulated change with a change in the eye tissue to be achieved;
   d') if step c') yields a sufficient agreement between the simulated change and the change in the eye tissue to be achieved, choose the auxiliary control program that includes the treatment parameters applied in step b') as the control program to be generated; and
   e') if in step c') the comparison does not yield a sufficient agreement between the simulated change and the change in the eye tissue to be achieved, modify at least one of the treatment parameters in step b') and repeat steps b'), c') and d').

12. A computer-implemented method for generating a control program for controlling electromagnetic radiation for cross-linking in eye tissue of a patient with a photosensitiser introduced into the eye tissue to change the eye tissue with reference to at least one of (A) its form, or (B) at least one of its mechanical properties, the computer implemented method comprising:
   a) receiving, with at least one computer, measurement data with reference to the both the patient and the eye;
   b) determining, with the at least one computer, a simulated change in the eye tissue by a computer based on the measurement data and the treatment parameters, the treatment parameters being parameters of a predetermined auxiliary control program for controlling a source of the electromagnetic radiation, the act of determining a simulated change in the eye tissue including
      determining a distribution of the photosensitiser by simulating a diffusion of the photosensitiser, and
      determining a depth-dependent absorption of the radiation on the basis of the simulated distribution of the photosensitiser;
   c) determining, with the at least one computer, whether or not the simulated change in the eye tissue is within a predetermined acceptable range of the change in the eye tissue to be achieved; and
   d) responsive to a determination that the simulated change in the eye tissue is within the predetermined acceptable range of the change in the eye tissue to be achieved, generating, with the at least one computer, the control program using the treatment parameters applied in step (b), and otherwise, responsive to a determination that the simulated change in the eye tissue is not within the predetermined acceptable range of the change in the eye tissue to be achieved, modifying, with the at least one computer, at least one of the treatment parameters in step (b), and repeating steps (b)-(d).

* * * * *